United States Patent
Hincapie Ordonez et al.

(10) Patent No.: US 8,942,819 B2
(45) Date of Patent: Jan. 27, 2015

(54) AUTOMATIC NEURAL STIMULATION TITRATION SWEEP

(75) Inventors: Juan Gabriel Hincapie Ordonez, Maple Grove, MN (US); Stephen Ruble, Lino Lakes, MN (US); Jason J. Hamann, Blaine, MN (US); Eric A. Mokelke, White Bear Lake, MN (US); Shantha Arcot-Krishnamurthy, Vadnais Heights, MN (US); Kevin John Stalsberg, White Bear Lake, MN (US); David J. Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 252 days.

(21) Appl. No.: 13/155,549

(22) Filed: Jun. 8, 2011

(65) Prior Publication Data
US 2011/0313488 A1 Dec. 22, 2011

Related U.S. Application Data

(60) Provisional application No. 61/355,272, filed on Jun. 16, 2010.

(51) Int. Cl.
*A61N 1/00* (2006.01)
*A61N 1/36* (2006.01)

(52) U.S. Cl.
CPC ........ *A61N 1/36142* (2013.01); *A61N 1/36146* (2013.01); *A61N 1/36114* (2013.01); *A61N 1/36139* (2013.01)
USPC ................................................ 607/63; 607/9

(58) Field of Classification Search
CPC ........... A61N 1/36146; A61N 1/36142; A61N 1/36139
USPC .................................................. 607/2, 9, 63
See application file for complete search history.

(56) References Cited

U.S. PATENT DOCUMENTS 5,222,494 A 6/1993 Baker, Jr.
5,916,239 A 6/1999 Geddes et al.
(Continued)

FOREIGN PATENT DOCUMENTS

AU 2011268043 B2 1/2014
JP 2009505737 A 2/2009
(Continued)

OTHER PUBLICATIONS

"International Application Serial No. PCT/US2011/039549, International Preliminary Report on Patentability mailed Jan. 3, 2013", 12 pgs.
(Continued)

*Primary Examiner* — Niketa Patel
*Assistant Examiner* — William Levicky
(74) *Attorney, Agent, or Firm* — Schwegman Lundberg & Woessner, P.A.

(57) ABSTRACT

Various neural stimulator embodiments comprise controller circuitry, neural stimulation output circuitry, sensor circuitry and a memory. The neural stimulation output circuitry is configured to deliver the neural stimulation. The controller circuitry is configured to control stimulation parameters of the neural stimulation delivered by the neural stimulation output circuitry. The sensor circuitry, including at least one sensor, is configured to sense a response to the neural stimulation. The controller is configured to communicate with the sensor circuitry. The memory has instructions stored therein, operable on by the controller circuitry. The instructions include instructions for delivering neural stimulation using the neural stimulation output circuitry, instructions for controlling a titration sweep wherein the titration sweep varies stimulation parameter values, and instructions for monitoring a response to the titration sweep and automatically selecting stimulation parameters that provide an efficacious neural stimulation and provide a desirable safety margin to prevent injury to neural tissue.

20 Claims, 9 Drawing Sheets

(56) References Cited

U.S. PATENT DOCUMENTS

| | | |
|---|---|---|
| 6,463,328 B1 | 10/2002 | John |
| 6,922,589 B2 | 7/2005 | Stahmann et al. |
| 7,096,064 B2 * | 8/2006 | Deno et al. .................... 607/9 |
| 7,551,958 B2 | 6/2009 | Libbus et al. |
| 7,747,318 B2 | 6/2010 | John et al. |
| 7,751,884 B2 | 7/2010 | Ternes et al. |
| 7,801,604 B2 | 9/2010 | Brockway et al. |
| 7,881,782 B2 | 2/2011 | Libbus et al. |
| 8,600,505 B2 | 12/2013 | Libbus et al. |
| 2003/0176894 A1 | 9/2003 | Stahmann et al. |
| 2004/0111041 A1 | 6/2004 | Ni et al. |
| 2004/0199210 A1 | 10/2004 | Shelchuk |
| 2005/0149127 A1 | 7/2005 | Libbus |
| 2006/0127366 A1 | 6/2006 | Mitrani et al. |
| 2006/0135998 A1 | 6/2006 | Libbus et al. |
| 2006/0161209 A1 | 7/2006 | Pastore et al. |
| 2006/0190053 A1 | 8/2006 | Dobak |
| 2006/0271108 A1 | 11/2006 | Libbus et al. |
| 2007/0049982 A1 * | 3/2007 | Cao et al. .................... 607/27 |
| 2007/0093870 A1 * | 4/2007 | Maschino .................... 607/2 |
| 2008/0004053 A1 | 1/2008 | Kim et al. |
| 2008/0058872 A1 * | 3/2008 | Brockway et al. ............ 607/2 |
| 2008/0058873 A1 | 3/2008 | Lee et al. |
| 2008/0058892 A1 | 3/2008 | Haefner et al. |
| 2008/0177356 A1 | 7/2008 | Greenberg et al. |
| 2009/0228079 A1 | 9/2009 | Libbus |
| 2010/0023090 A1 | 1/2010 | Jaax et al. |
| 2010/0121408 A1 * | 5/2010 | Imran et al. .................... 607/46 |
| 2010/0222844 A1 | 9/2010 | Troosters et al. |
| 2010/0228310 A1 | 9/2010 | Shuros et al. |
| 2010/0234912 A1 | 9/2010 | Ternes et al. |
| 2010/0236062 A1 | 9/2010 | Greenberg et al. |
| 2011/0015702 A1 | 1/2011 | Ternes et al. |
| 2011/0015703 A1 | 1/2011 | Ternes et al. |
| 2011/0245890 A1 * | 10/2011 | Brisben et al. .................. 607/28 |

FOREIGN PATENT DOCUMENTS

| | | |
|---|---|---|
| JP | 2013528467 A | 7/2013 |
| WO | WO-0245791 A2 | 6/2002 |
| WO | WO-2004034880 A2 | 4/2004 |
| WO | WO-2007127443 A2 | 11/2007 |
| WO | WO-2009046764 A1 | 4/2009 |
| WO | WO-2011159527 A2 | 12/2011 |
| WO | WO-2011159527 A3 | 12/2011 |

OTHER PUBLICATIONS

"International Application Serial No. PCT/US2011/039549, International Search Report mailed Dec. 19, 2011", 6 pgs.

"International Application Serial No. PCT/US2011/039549, Invitation to Pay Additional Fees mailed Sep. 14, 2011", 10 pgs.

"International Application Serial No. PCT/US2011/039549, Written Opinion mailed Dec. 19, 2011", 11 pgs.

"Japanese Application Serial No. [Pending], Amendment filed Feb. 19, 2013", 3 pgs.

McCreery, D.B., et al., "Stimulus Parameters affecting tissue injury during microstimulation in the cochlear nucleus of the cat", Hearing Research, Elsevier Science, vol. 77, No. 1-2, (Jun. 15, 1994), 105-115.

"Japanese Application Serial No. 2013-515381, Office Action mailed Feb. 5, 2014", With English Translation, 3 pgs.

* cited by examiner

AUTOMATIC NEURAL STIMULATION TITRATION SWEEP

CLAIM OF PRIORITY

This application claims the benefit of priority under 35 U.S.C. §119(e) of U.S. Provisional Patent Application Ser. No. 61/355,272, filed on Jun. 16, 2010, which is herein incorporated by reference in its entirety.

TECHNICAL FIELD

This application relates generally to medical devices and, more particularly, to systems, devices and methods for sweeping through potential parameter combinations for an implantable medical device therapy and selecting a desirable combination of the therapy parameters.

BACKGROUND

Implantable Medical Devices (IMDs) have been designed or proposed to treat various conditions. For example, some IMDs are designed to treat cardiac conditions and perform functions such as pacing, cardioversion and defibrillation. Some IMDs deliver neural stimulation. By way of example and not limitation, neural stimulation has been proposed as a therapy for respiratory problems such as sleep disordered breathing, blood pressure control such as to treat hypertension, cardiac rhythm management, myocardial infarction and ischemia, heart failure, epilepsy, depression, pain, migraines, eating disorders, obesity, inflammatory diseases, and movement disorders.

NeuroCardiac Therapy (NCT), as used herein, refers to neural stimulation delivered for a cardiovascular therapy. NCT, by way of example and not limitation, includes the stimulation of an autonomic neural target to provide a therapy for a cardiac arrhythmia, ischemia, heart failure, angina, atherosclerosis, blood pressure, and the like. By way of example and not limitation, autonomic neural targets used to deliver NCT include the vagus nerve, cardiac branches of the vagal nerves, baroreceptors, chemoreceptors, cardiac fat pads, the spinal column or some nerve roots extending from the spinal column.

SUMMARY

Various neural stimulator embodiments comprise controller circuitry, neural stimulation output circuitry, sensor circuitry and a memory. The neural stimulation output circuitry is configured to deliver the neural stimulation. The controller circuitry is configured to control stimulation parameters of the neural stimulation delivered by the neural stimulation output circuitry. The sensor circuitry, including at least one sensor, is configured to sense a response to the neural stimulation. The controller is configured to communicate with the sensor circuitry. The memory has instructions stored therein, operable on by the controller circuitry. The instructions include instructions for delivering neural stimulation using the neural stimulation output circuitry, instructions for controlling a titration sweep wherein the titration sweep varies stimulation parameter values, and instructions for monitoring a response to the titration sweep and automatically selecting stimulation parameters that provide an efficacious neural stimulation and provide a desirable safety margin to prevent injury to neural tissue.

Various embodiments provide a method for programming neural stimulation parameters into a neural stimulator. Neural stimulation is delivered to a neural target. The neural stimulation has a plurality of stimulation parameters. A titration sweep for the neural stimulation is performed. Performing the titration sweep includes varying values for the plurality of stimulation parameters. One or more physiological responses may be monitored to determine stimulation efficacy for the various parameter values. The method includes determining desirable parameter values that provide efficacious neural stimulation and that have a desirable stimulation safety margin to avoid injury to neural tissue, and programming the neural stimulator with the parameter values that provide efficacious neural stimulation and that have the desirable stimulation safety margin.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1:
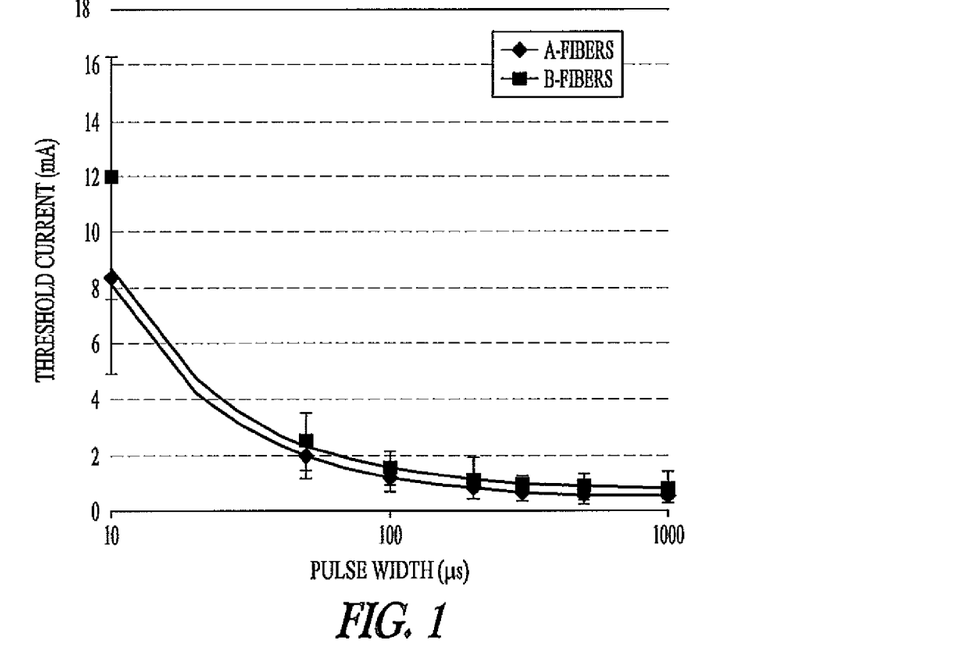
FIG. 1 illustrates a plot, known as the strength-duration curve, of threshold current, in milliamps, against the pulse width of the stimulation current for both A and B nerve fibers.

Nerve recruitment, effectiveness and neural safety depend on charge delivered and charge density (current amp×pulse width/electrode area). For example, FIG. 1 illustrates a plot, known as the strength duration curve, of threshold current, in milliamps, against the pulse width of the stimulation current for both A and B nerve fibers. The threshold current is reduced as the pulse width of the stimulation pulse increases. However, safety and patient tolerance for the therapy limit the charge density that can be delivered. The present subject matter provides an automatic neural stimulation titration sweep to find a combination of therapy parameters (such as amplitude, pulse width, duty cycle) that provides a tolerable and safe dose for a particular patient. For example, some embodiments attempt to determine an effective dose while maximizing the tolerance and safety of the effective dose or while maintaining an adequate or desired margin for tolerance and safety of the effective dose.

Prolonged neural stimulation can cause damage in the peripheral/central nervous system, and electrode-induced neural damage is a concern as the therapy should be delivered in a safe manner. The amount of charge that can be injected into neural tissue without causing harm ("safety limit") has been referred to as the charge injection limit or charge density limit. Studies have been performed in several animal models to help establish neural stimulation safety limits for neural stimulation.

The charge per phase and charge density per phase are important parameters for neural stimulation-induced damage. Charge density per phase and charge per phase are related to current density and total injected current respectively. Charge per phase (Q) is the total volume within which the neurons are excited and is measured in C/phase. Where I is electrical current amplitude and I is time the current was delivered, the charge per phase (Q) can be expressed as:

$$Q = It.$$

Charge density per phase (QD) determines the proportion of neurons close to an electrode that are excited. The charge density per phase (QD) can be calculated as the ratio of the charge per phase to the surface area of the electrode (coulomb/area-phase):

$$QD = \frac{It}{SA}.$$

This equation calculates average charge density. It has been reported that there is charge accumulation near the edges of the interface between the electrode and tissue. Charge density is a function of several variables, including the amount of current delivered, the surface area of the stimulating electrode, and the pulse width. Charge density (QD) can be expressed with the units "microcoulombs/cm$^2$/phase."

Currently, there are no guidelines that specifically address neurostimulation systems. Rather, each device requires its own safety studies, which are then reviewed by the regulatory bodies. However, literature on neural safety indicates that a combination of parameters whose charge injection limit exceeds approximately 40 microcoulombs/cm$^2$/phase can cause neural damage. Some neurostimulation devices that are currently approved for clinical use have 30 μC/cm$^2$/phase as a safe upper bound when stimulating nervous tissue. This 30 μC/cm$^2$/phase limit is not an established requirement, but rather a suggested safety margin. Programming a device to deliver stimulation above this level could potentially cause tissue damage.

Figure 2:
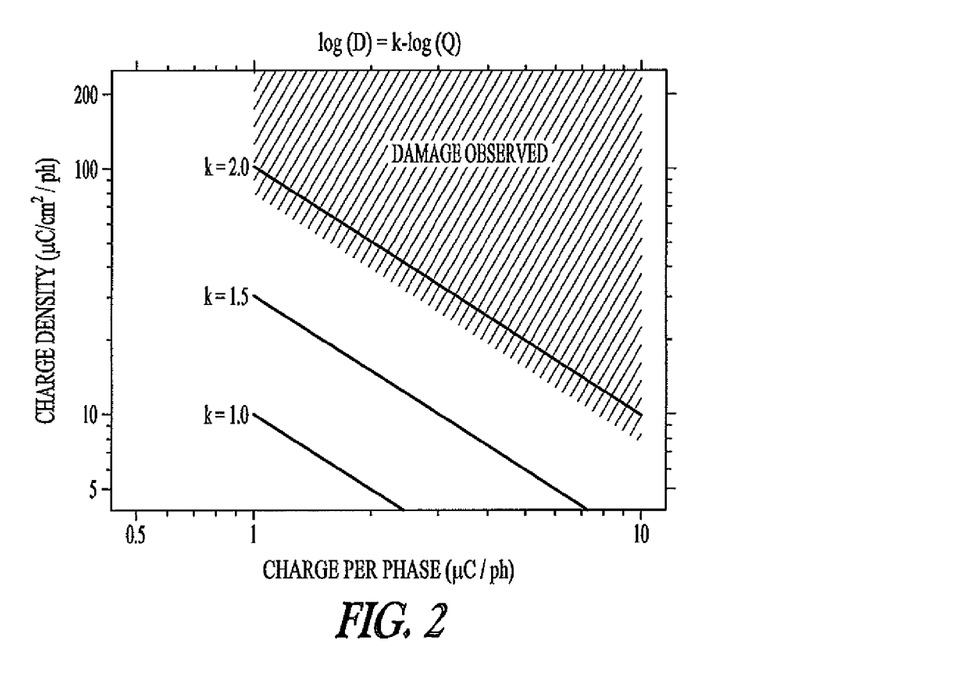
FIG. 2 illustrates a plot of the charge density against charge per phase for several safety margins ("k" values) of 1.0, 1.5 and 2.0.

It has been reported that the boundary between safe charge injections at different charge and charge density could be approximated by the equation:

$$\log QD = k - \log Q$$

where "k" is a constant whose value changes the intercept of the line and at a certain value. Safe and unsafe zones have been determined by experimental work under different conditions, species, neural targets and stimulation electrodes. Generally, the area to the right of the "k" line is considered unsafe since experiments that observed damage fell in the area. The equation is referred to as the Shannon equation, which is a generally accepted mathematical approach to calculating safety limits for neurostimulation. Conservative values for "k" lie between 1.7 and 2. FIG. 2 illustrates a plot of the charge density against charge per phase for several safety margins ("k" values) of 1.0, 1.5 and 2.0. This plot illustrates that damage may occur for "k" values higher than 1.8.

If a device that is coupled to a nerve cuff is programmed to the highest output, the resulting stimulation may exceed the charge injection limits (the limit at which neural damage can occur). Neural damage might occur if a device that is coupled to a nerve cuff is programmed to a level of stimulation that exceeds the charge injection limit and the device has no programming restriction above the safe levels.

Figure 3:
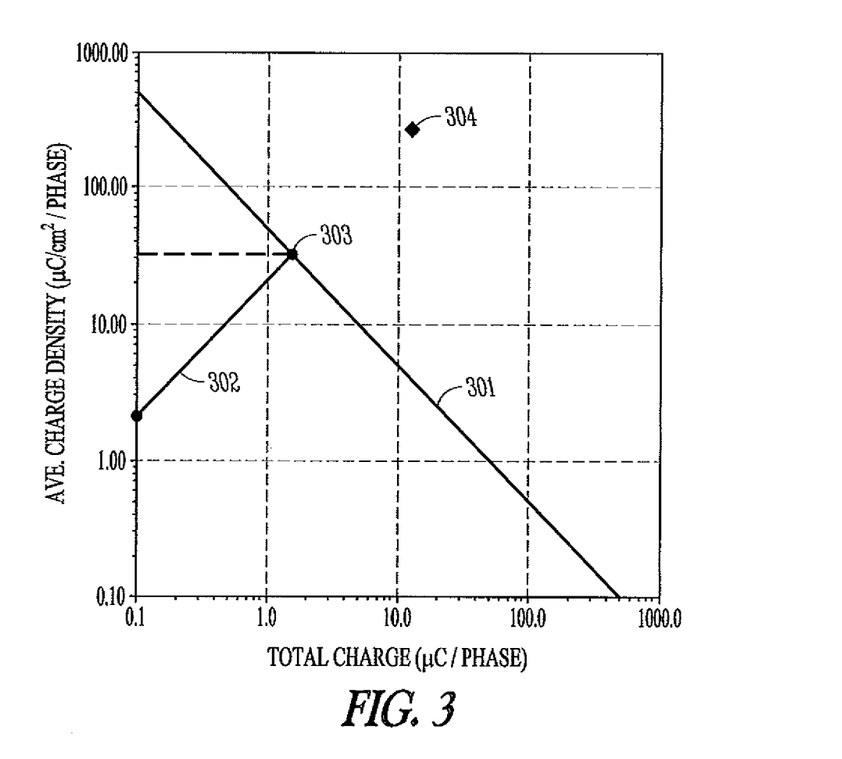
FIG. 3 illustrates a plot of the average charge density against total charge.

FIG. 3 illustrates a plot of the average charge density against total charge. Line 301 illustrates the safe stimulation threshold for a "k" value and line 302 illustrates a relationship between the average charge density and total charge as the amplitude of the stimulation signal increases. The point 303 where line 302 crosses the safe stimulation threshold 301 provides a safe limit for the average charge density and the safe limit for the total charge. An example of a combination of stimulation parameters that will potentially be unsafe is illustrated at Point 304 in FIG. 3.

From Shannon's equations:

$$\log(QD) + \log(Q) = k,$$
$$QD = \frac{I \times t}{SA},$$
$$Q = I \times t,$$
$$\log\left(\frac{I \times t}{SA}\right) = k - \log(I \times t),$$
$$I \times t = (SA \times 10^k)^{0.5}.$$

These equations can be used to calculate the current required to cross a certain value of k.

In an example, an electrode has a surface area of 0.06 cm$^2$, and the stimulation is delivered at a 2 mA current and a pulse width of 300 μsec.

Charge:
$$Q = I \times t,$$
$$Q = 2 \text{ mA} \times 300 \text{ μsec} = 0.6 \text{ μC/phase}.$$

Charge Density:
$$QD = (I \times t)/SA,$$
$$QD = \frac{2 \text{ mA} \times 300 \text{ μsec}}{0.06 \text{ cm}^2} = 10 \text{ μC/cm}^2 - \text{phase}.$$

For a pulse width of 300 μsec with k=1.7, $$I \times t = (SA \times 10^k)^{0.5},$$
$$I = \frac{(0.06 * 10^{1.7})^{0.5}}{300 \text{ μsec}},$$
$$I = 5.78 \text{ mA}.$$

Neural stimulation is challenging to quantify because of the time varying pattern of the stimulation waveform. By way of example and not limitation, a neural stimulation waveform could be sinusoidal or pulsatile. Current-controlled stimulation is commonly used to control the amount of charge delivered since it is not dependent on the varying tissue-electrode impedance. For example, biphasic charge-balanced pulsatile waveforms may be used to deliver NCT and other neural stimulation therapies. Pulsatile waveforms are essentially periodic trains of pulses that usually have equal amplitude. There is no net direct current (DC) for these pulsatile waveforms. Direct current may cause damage to the neural tissue.

Figure 4:
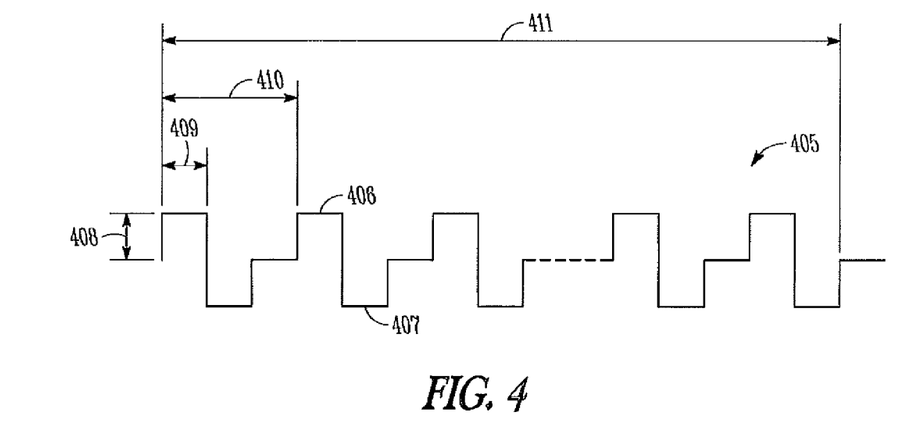
FIG. 4 illustrates biphasic current waveform.

FIG. 4 illustrates biphasic current waveform 405. A biphasic current waveform has two consecutive pulse phases that have equal charge but opposite polarity and no net DC component. These consecutive pulse phases may be referred to as a stimulating phase 406 and a reversal phase 407. The stimulating phase 406 elicits the desired physiological response such as initiation/suppression of the physiological response and the reversal phase 407 recovers the charge that was delivered during the first phase. This symmetry is intended to cause no net production of any electrolytic products in the solution. Some charge-delayed waveform embodiments provide a brief delay in the pulses. Pre-clinical studies have shown that low levels of unbalanced wave forms such as monophasic stimulation can cause vasoconstriction, thrombosis of venules and arterioles and breakdown of the blood-brain barrier within 30 seconds of stimulation (cerebral cortex of cat), but no tissue damage was found up to hours of continuous stimulation with biphasic charge balanced stimulation when the charge density was below 4.5 $\mu C/cm^2$). FIG. 4 also illustrates the amplitude 408 of the simulating phase, a phase or pulse width 409 of the stimulating phase, the pulse period 410 of a biphasic pulse which is the inverse of the pulse frequency, and the neural stimulation burst duration 411. The neural stimulation burst comprises a train of neural stimulation pulses.

Figure 5:
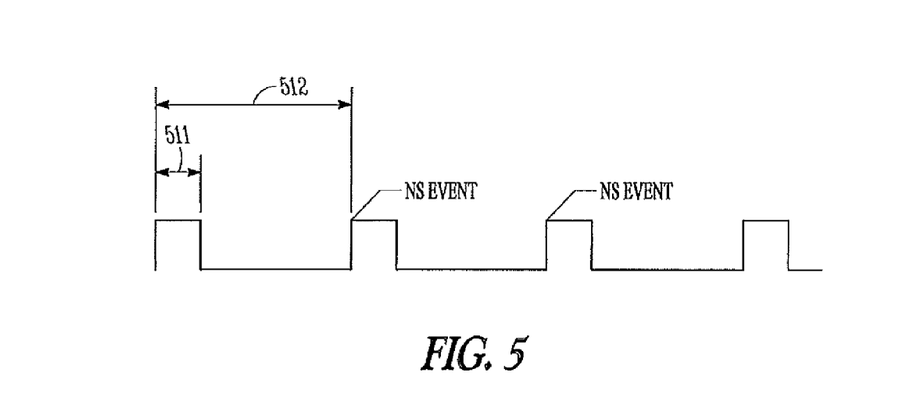
FIG. 5 illustrates a representation of intermittent neural stimulation (INS).

FIG. 5 illustrates a representation of intermittent neural stimulation (INS). The figure diagrammatically shows the time-course of a neural stimulation that alternates between intervals of stimulation being ON, when one stimulation pulse or a set of grouped stimulation pulses (i.e., a burst 511) is delivered, and intervals of stimulation being OFF, when no stimulation pulses are delivered. Thus, for example, some embodiments deliver a plurality of pulses such as the biphasic pulses illustrated in FIG. 4 within a neural stimulation burst illustrated in FIG. 5. The duration of the stimulation ON interval is sometimes referred to as the stimulation duration or burst duration. The start of a stimulation ON interval is a temporal reference point NS Event. The time interval between successive NS Events is the INS Interval, which is sometimes referred to as the stimulation period or burst period 512. For an application of neural stimulation to be intermittent, the stimulation duration (i.e., ON interval) must be less than the stimulation period (i.e., INS Interval) when the neural stimulation is being applied. The duration of the OFF intervals of INS are controlled by the durations of the ON interval and the INS Interval. The duration of the ON interval relative to the INS Interval (e.g., expressed as a ratio) is sometimes referred to as the duty cycle of the INS.

Figure 6A:
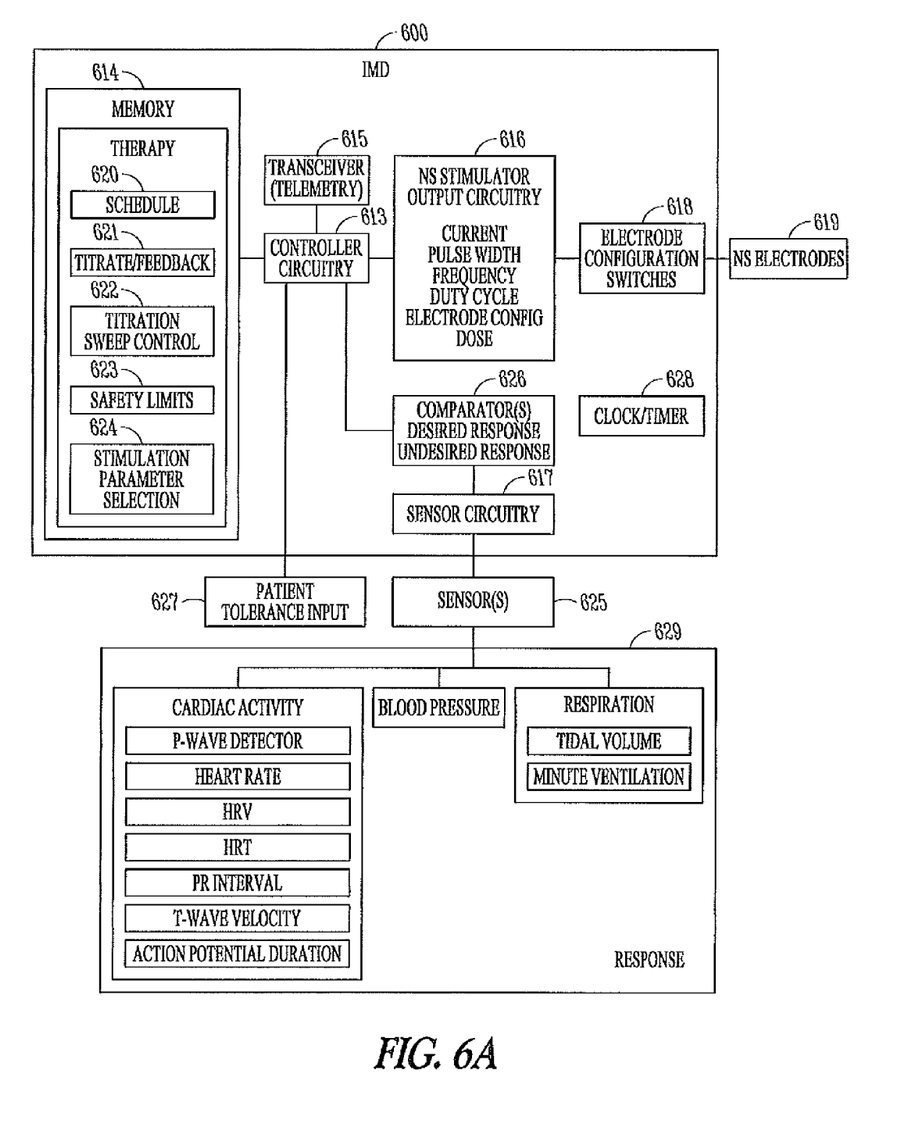
FIGS. 6A-B illustrate embodiments of a neural stimulator.
Figure 6B:
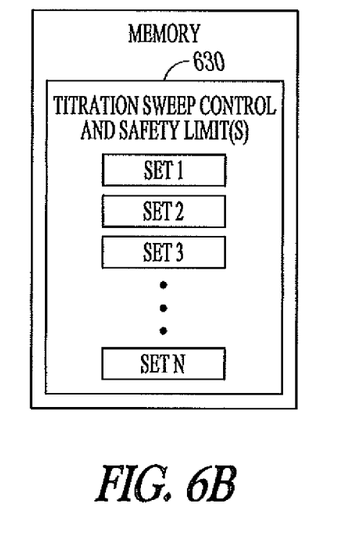

FIGS. 6A-B illustrate embodiments of a neural stimulator 613. The illustrated neural stimulator 600 provides neural stimulation signals for delivery to predetermined neural targets. The illustrated device includes controller circuitry 613 and memory 614. The controller circuitry is capable of being implemented using hardware, software, firmware or combinations thereof. For example, according to various embodiments, the controller circuitry includes a processor to perform instructions embedded in the memory to perform functions associated with the neural stimulation therapy, including instructions for performing a titration sweep and automatically selecting a desired neural stimulation parameter set that provides effective neural stimulation and that has a desirable safety margin. The illustrated device further includes a transceiver 615 and associated circuitry for use to communicate with a programmer or another external or internal device. Various embodiments have wireless communication capabilities. For example, some transceiver embodiments use a telemetry coil to wirelessly communicate with a programmer or another external or internal device.

The illustrated device further includes neural stimulation output circuitry 616 and sensor circuitry 617. According to some embodiments, one or more leads are able to be connected to the sensor circuitry and neural stimulation circuitry. Some embodiments use wireless connections between the sensor(s) and sensor circuitry, and some embodiments use wireless connections between the stimulator circuitry and electrodes. According to various embodiments, the neural stimulation circuitry is used to apply electrical stimulation pulses to desired neural targets, such as through one or more stimulation electrodes 619 positioned at predetermined location(s). Some embodiments use transducers to provide other types of energy, such as ultrasound, light or magnetic energy. In various embodiments, the sensor circuitry 617 and sensor(s) are used to detect physiological responses. The controller circuitry can control the therapy provided by the system using a therapy schedule and/or a therapy titration routine. Some embodiments compare a target range (or ranges) of the sensed physiological response(s) stored in the memory 614 to the sensed physiological response(s) to appropriately adjust the intensity of the neural stimulation signal.

Some embodiments are adapted to change a stimulation signal feature, the neural stimulation target and/or change the neural stimulation vector as part of a neural stimulation titration routine. The stimulation output circuitry 616 is adapted to set or adjust any one or any combination of stimulation features based on commands from the controller circuitry 613. Examples of stimulation signal features include the current amplitude, pulse width, frequency, duty cycle and dose. Some embodiments are adapted to change electrode configuration as part of the neural stimulation titration routine. The illustrated embodiment includes electrode configuration switches 618, and the switches are configured to deliver neural stimulation from the output circuitry 616 to selected neural stimulation electrodes 619. In the illustrated embodiment, the neural stimulation output circuitry 616 is configured to control the switches to provide the desired electrode configuration. In some embodiments, the controller circuitry 613 is configured to control the switches 618.

In an embodiment, the controller circuitry 613 is programmed to control the neural stimulation delivered by the stimulation output circuitry 616 according to stimulation instructions, such as a stimulation schedule 620, stored in the memory 614. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be composed of multiple burst durations and burst interval sequences. The programmed pattern of bursts can be characterized by a duty cycle, which refers to a repeating cycle of neural stimulation ON for a fixed time and neural stimulation OFF for a fixed time.

The illustrated memory 614 includes instructions 621, operable on by the controller circuitry 613, to receive therapy feedback and titrate the therapy based on the feedback. The illustrated memory 614 includes instructions 622, operable on by the controller circuitry 613, to control a titration sweep. During the titration sweep, the neural stimulation signal is delivered using different combinations of stimulation parameters, and the effects of the stimulation are evaluated for the different parameter combinations. The illustrated memory 614 includes instructions 623, operable on by the controller circuitry 613, to determine the safety limits for the various stimulation parameters. For example, the safety limits can be determined using Shannon's equation. The illustrated memory 614 includes instructions 624, operable on by the controller circuitry 613, to select the combination of stimulation parameters that is determined to be effective at generating the desired physiological effect and that has a desirable safety margin.

The sensor circuitry 617 and sensor(s) 625 are used to detect a physiological response 629. The detected response can be cardiac activity or surrogates of cardiac activity such as blood pressure and respiration measurements. Examples of physiological responses include cardiac activity such as heart rate, HRV, PR interval, T-wave velocity, and action potential duration. Other examples of physiological responses include hemodynamic responses such as blood pressure, and respiratory responses such as tidal volume and minute ventilation. Examples of cardiac activity include a heart rate, HRV, PR interval, T-wave velocity, and action potential duration. Some embodiments monitor hemodynamic responses such as blood pressure, and some embodiments monitor respiratory responses such as tidal volume and minute ventilation. The monitored physiologic variables are selected to monitor effects of the neural stimulation. For example, the stimulation of an autonomic neural target such as the vagus nerve or a branch thereof may affect heart rate, blood pressure and respiration. A comparator 626 compares the sensed physiological response to a target range stored in the memory, and the controller circuitry 613 receives a comparison result and controls the neural stimulation based on the comparison in an attempt to keep the response within the target range. In some embodiments, the function of the comparator is performed within the controller circuitry 613. The target range stored in the memory can be programmable. The detected physiological response(s) are tracked during titration sweeps to determine which stimulation parameter sets delivered during the sweep provide a desired physiological response. Some embodiments use more than one feedback. For example, some embodiments require a change in one parameter, and require no change or a change within limits in another parameter.

According to various embodiments, the controller is configured to respond appropriately to a patient tolerance input 627. The patient or a clinician may provide the patient tolerance input. For example, a clinician may enter a value for patient tolerance into a programmer during the programming or adjustment of the neural stimulator, or an ambulatory patient may enter a value for patient tolerance in a portable device. The programmer or portable device is capable of directly or indirectly communicating with the neural stimulator. Examples of patient tolerance inputs include inputs that indicate that the patient is experiencing cough, pain, a scratchy throat, a voice change, and/or swallowing issues.

The illustrated device includes a clock or timer/counter 628 which can be used to execute the programmable stimulation schedule. For example, a physician can program a daily schedule of therapy based on the time of day. A stimulation session can begin at a first programmed time, and can end at a second programmed time. Various embodiments initiate and/or terminate a stimulation session based on a signal triggered by a user. Various embodiments use sensed data to enable and/or disable a stimulation session.

FIG. 6B illustrates a memory for the implantable medical device illustrated in FIG. 6A, wherein the memory includes instructions 630, operable on by the controller circuitry 613, for controlling a titration sweep by sweeping through defined parameter sets (e.g. parameter set 1 through parameter set N). The defined parameter sets available during the titration sweep are chosen to be within the safety limits. Thus, the instructions 630 with the defined parameter sets can be used in place of the instructions 622 and 623 used to control the titration sweep and to determine the safety limits for the different parameter combinations that occur during the titration sweep.

The instructions in the memory may include instructions for calculating a safety limit for the stimulation parameters, and confirming that the charge per phase and charge density per phase does not violate the safety limit, as generally illustrated in FIG. 6A. The memory may include a plurality of neural stimulation parameter sets, where each set includes a unique combination of parameter values for the neural stimulation and wherein each unique combination of parameter values is defined to provide a charge per phase and charge density per phase that avoids damage to the neural tissue. The instructions for controlling the titration sweep includes instructions for stepping through the plurality of neural stimulation parameter sets.

The embodiments of titration sweep processes discussed below may be initiated by a clinician within a clinical setting, may be automatically initiated periodically (e.g. daily or weekly) or according to another programmed schedule, or may be triggered by a patient or clinician when the patient is ambulatory away from the clinical setting. For example, an undesirable side effect, such as an undesired cough, an undesired change in heart rate or blood pressure, or pain may trigger a titration sweep.

Various embodiments provide a neural stimulation parameter titration sweep that automatically finds the desirable combination of therapy parameters (e.g. amplitude, pulse width, duty cycle) that provides a tolerable and a safe dose for a particular patient. Some titration sweep embodiments are initiated manually by a clinician or by a patient. Some titration sweep embodiments are periodically or intermittently initiated by the device according to a programmed schedule. Some titration sweep embodiments are triggered based on a sensed physiological parameter. For example, an undesirable side effect, such as an undesired cough, an undesired change in heart rate or blood pressure, or pain may trigger a titration sweep. The parameter combinations that are evaluated during the sweep could range from a limited parameter set determined by design or clinician input, up to a full suite of all available parameter combinations. The order of the parameters in the sweep may be predetermined by design or clinician input. Some embodiments weigh patient input such as weighing of side-effect tolerance.

Some embodiments step through "n" potential parameter selection sets to determine a desirable program parameter set. The system may be programmed to control the specific order for evaluating the potential parameter sets. For example, after a parameter set is evaluated, the parameter set variable can be incremented to evaluate the next parameter set. In another embodiment, the system is programmed to randomly evaluate the parameter selection sets. It is believed that the random evaluation may reduce the potential that a specific order for evaluating the parameter selection sets obscures the results.

Figure 7:
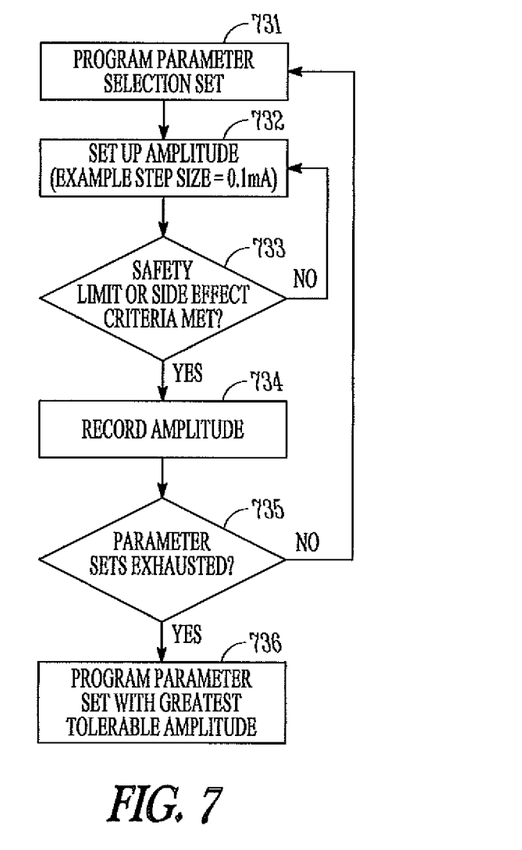
FIGS. 7-9 illustrate method embodiments for performing a titration sweep and for selecting stimulation parameters.
Figure 8:
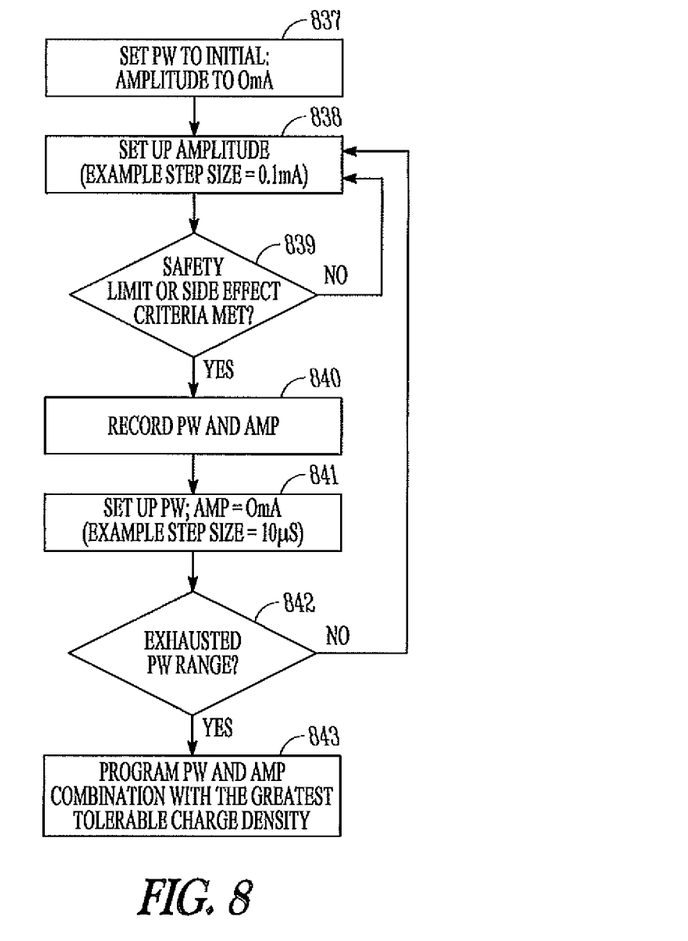
Figure 9:
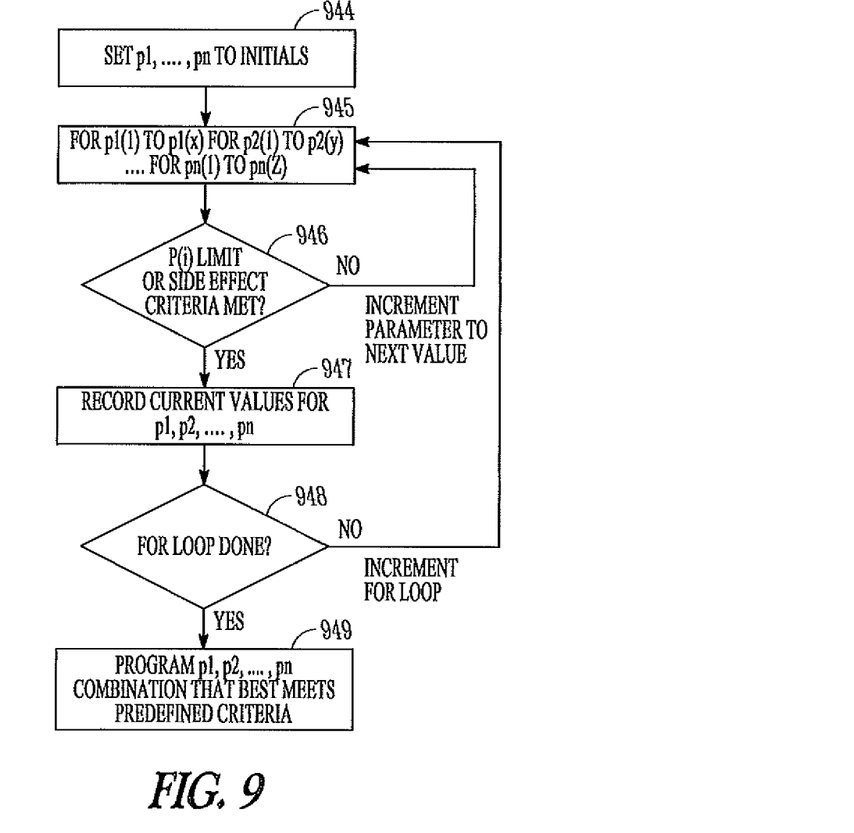

FIGS. 7-9 illustrate method embodiments for performing a titration sweep and for selecting stimulation parameters. In FIG. 7, a parameter selection set is programmed into the device at 731. The device is configured to deliver the neural stimulation using the programmed selection set. The amplitude of the stimulation is stepped up at 732. For example, the amplitude of the stimulation may be stepped up by a current value of 0.1 mA. Other step sizes are within the scope of the present subject matter. At 733, it is determined if criteria for a side effect or criteria for a safety limit has been met. If the criteria has not been, met, then the process returns to 732 to step up the stimulation amplitude again. If the criteria has been met, the process proceeds to 734 to record the amplitude. At 735, it is determined whether the parameter sets have been exhausted (all available parameter sets capable of being evaluated have been evaluated). If the parameter sets have not been exhausted, then the process returns to 731 to program the device with the new parameter selection set. If the parameter sets have been exhausted, then at 736 the parameter set with the greatest tolerable amplitude is programmed into the device.

In FIG. 8, the pulse width and the amplitude are set to initial values at 837. For example, the amplitude can be set to 0.0 mA. At 838 the amplitude is stepped up by an increment. At 839, it is determined whether a safety limit or side effect criteria has been met. If the criteria has not been met, the process returns to 838 to step up the amplitude by another increment. If the criteria has been met, the pulse width and amplitude is recorded at 840, and at 841 the pulse width is stepped up by an increment (e.g. 10 μS) and the amplitude is returned to the initial value (e.g. 0.0 mA). At 842, it is determined if the pulse width range has been exhausted. If the pulse width range has not been exhausted, the process returns to 838 to step up the amplitude by an increment. If the pulse width range has been exhausted, the neural stimulation is programmed with a pulse width and amplitude that provides the greatest tolerable charge density at 843.

In FIG. 9 at 944, the stimulation parameters (p1, p2 ... pn) are set to initial values. As illustrated generally at 945, a number of loops are processed, where each parameter (p1, p2 ... pn) is stepped up through available values. In each loop, it is determined whether the limit or side effect has been met, as generally illustrated at 946. If the limit or side effect has not been met, the process returns to 945 to proceed to the next increment in the loop. If the limit or side effect has been met, then the current values for the parameters are recorded at 947. At 948, it is determined if the loop is complete. If the loop is not done, the process returns to 945 to increment the parameter values. If the loop is done, then at 949 the combination of parameters that best met the predefined criteria is programmed into the neural stimulator.

The P(i) Limit may be a maximum value in range for parameter value "i" or may be a safety limit for parameter value "i" in combination with the other parameters (e.g. charge density and total amount of charge delivered per time period). Potential parameters for P(i) include current amplitude, pulse width, frequency, dosing and electrode configuration. The predefined criteria may include the greatest tolerable current density, the greatest tolerable charge per time period, the best device longevity while delivering efficacious therapy (lower dose may be as efficacious as higher dose; higher dose/less frequent), or a stop when the stimulation is "good enough" rather than proceeding with a full sweep.

In an example, the safety limit corresponds to a charge density less than or equal to a given amount (e.g. CD≤25 μC/cm$^2$ or 30 μC/cm$^2$, etc.). Some embodiments monitor criteria for any one or any combination of potential side effects such as laryngeal vibration, cough, pain (e.g. input from patient), heart rate change, heart sounds/hemodynamics, AV delay change, QRS width change, ECG morphology change, blood pressure change, and the like.

Figure 10:
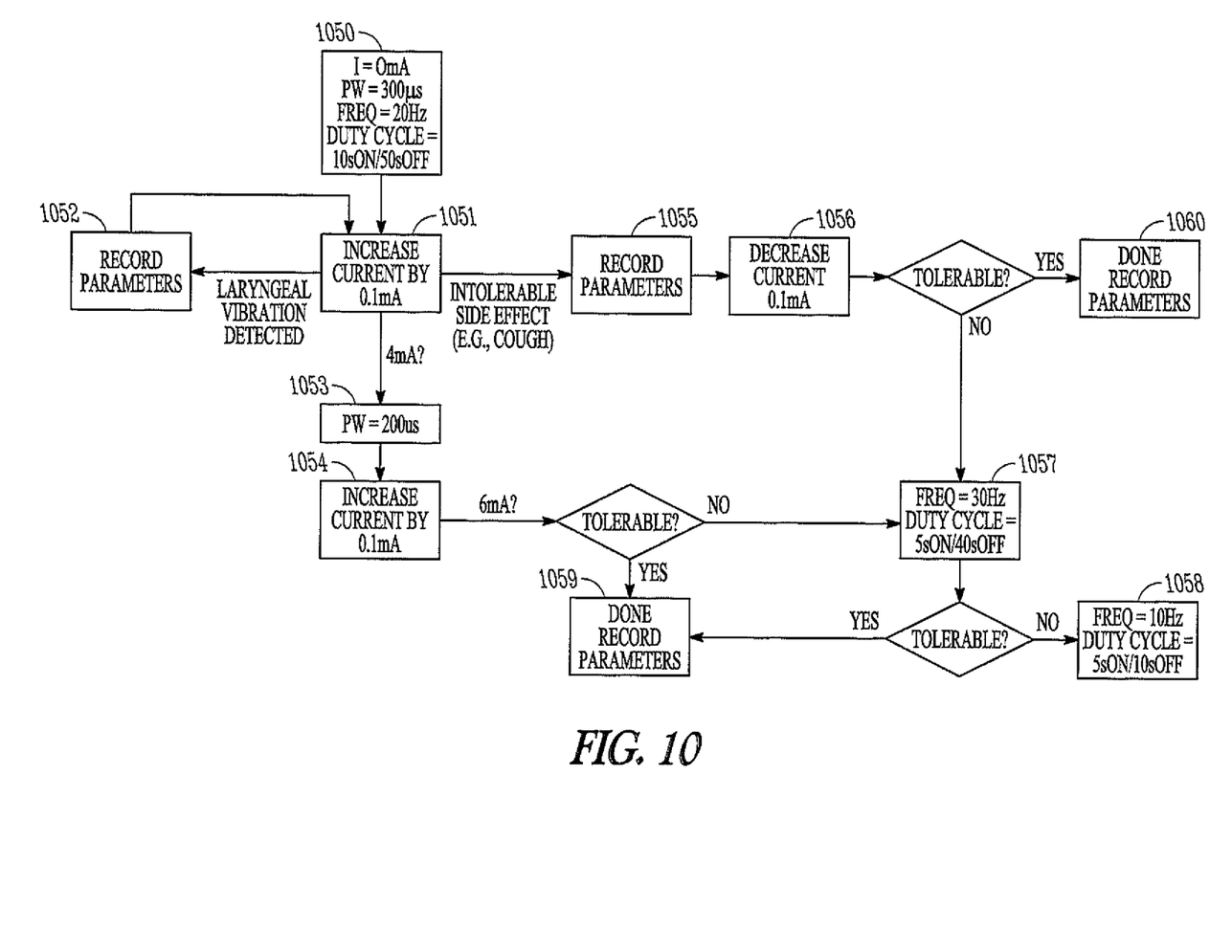
FIG. 10 illustrates an embodiment of a titration procedure.

FIG. 10 illustrates an embodiment of a titration procedure. The illustrated embodiment assumes that a higher dose results in increased therapy efficacy, assumes that nerve recruitment characteristics do not change considerably between pulse widths of 300 μs to 200 μs as illustrated in FIG. 1 where A and B fiber threshold of 200 μs and 300 μs are almost identical, that safety levels are maintained by not exceeding 25 μC/cm$^2$/phase, and assumes that the dose can be characterized by number of pulses delivered using solely frequency and duty cycle. The following relationships can be used to determine the charge density and daily dose.

$$CD(\mu C/cm^2/phase) = Current(I) * pulse\ width / Electrode\ Area$$

$$DD: Daily\ Dose(pulses/day) = Frequency * Duty\ Cycle * 60 * 60 * 24$$

Given a maximum charge density of 25 μC/cm$^2$/phase for safe stimulation and a minimum electrode area of 4.8 mm$^2$, the following table can be completed.

| PW (ms) | Max I (mA) | Freq (Hz) | Duty Cycle | Equivalent | DD (pulses/day) |
|---|---|---|---|---|---|
| 0.2 | 6 | 10 | 1/3 | 5 s ON/10 s OFF | 288000 |
| 0.2 | 6 | 20 | 1/6 | 10 s ON/50 s OFF | 288000 |
| 0.2 | 6 | 30 | 1/9 | 10 s ON/80 s OFF | 288000 |
| 0.3 | 4 | 10 | 1/3 | 5 s ON/10 s OFF | 288000 |
| 0.3 | 4 | 20 | 1/6 | 10 s ON/50 s OFF | 288000 |
| 0.3 | 4 | 30 | 1/9 | 10 s ON/80 s OFF | 288000 |

Safety may depend upon the daily dose. The table modifies the duty cycle of the stimulation to provide a consistent dose of 288,000 pulses per day. A greater charge density may lower the necessary daily dose. Additionally, a patient may find that a narrower pulse width with higher amplitude (and greater charge density) more tolerable than other combinations, or a patient may find different rates of ramp up more tolerable. The available parameter sets may be defined to account for the combination of charge density and daily dose and the patient tolerance.

The electrode properties can be configurable or automated to change the surface area for stimulation. In some embodiments, the safety limits are automatically populated and unsafe ranges locked out when the clinician inputs information or connects a specific electrode/lead.

The present subject matter provides a system that is capable of automatically finding a desirable combination of therapy parameters (e.g. amplitude, pulse width, duty cycle) that provides a tolerable and safe dose for a particular patient. Thus, by providing an easy-to-use system that improves efficacy via dose control and improves tolerance, the present subject may encourage quicker therapy acceptance and adoption.

Some embodiments of the present subject matter define a limited number of parameter sets. By way of example and not limitation, the set of parameter sets may include: Set 1: 300 μS PW, 20 Hz frequency, 0 mA, 10 sec ON/50 sec OFF; Set 2:

200 µS PW, 20 Hz frequency, 0 mA, 10 sec ON/50 sec OFF; Set 3: 300 µS PW, 30 Hz frequency, 0 mA, 5 sec ON/40 sec OFF; and Set 4: 200 µS PW, 30 Hz frequency, 0 mA, 5 sec ON/40 sec OFF. The 0 mA is an initial value for the current. The current is incremented during the titration sweep. By way of example and not limitation, each of the defined parameter sets can be associated with a defined safety limit, such as 4 mA for Set 1, 6 mA for Set 2, 4 mA for Set 3, and 6 mA for Set 4. Safety limits are specific to a particular electrode design, surface area and pulse width.

The example illustrated in FIG. 10 using the parameter values assumes that a higher dose results in greater therapy efficacy, that recruitment characteristics do not change considerably between parameter sets, that safety levels are maintained by algorithm, and that the dose can be characterized by number of pulses delivered.

At 1050, the initial values for the stimulation parameters are provided. In the illustrated example, initial values are provided for current, pulse width, frequency and duty cycle. The initial values correspond to set 1 in the example parameter sets. At 1051, the current is increased by an increment. If laryngeal vibration is detected, the parameters are recorded at 1052 and the process returns to 1051 to increment the current. By way of example, laryngeal vibration is an early physiological response when the vagus nerve is stimulated. Thus, some embodiments use laryngeal vibration as a marker that the neural stimulation is having a physiological effect. If the current has reached 4 mA (the limit for Set 1 and a particular electrode design, surface area and pulse width in the illustrated example), the pulse width is adjusted at 1053 (e.g. reduced from 300 µs to 200 µs) to maintain safe stimulation. This generally corresponds to Set 2 in the illustrated example, and the current is incremented at 1054.

If the patient experiences intolerable side effects such as a cough, the parameters are recorded at 1055, and the current is reduced at 1056. If the stimulation still is not tolerable, then the process changes the frequency and duty cycle at 1057. Example Sets 3 and 4 both have a 30 Hz frequency. For example, Set 3, with a pulse width of 300 µS can be used, and the process returns to 1051 where the current is incremented until the current reaches 4 mA, at which time the process uses Set 4 with a pulse width of 200 µS. If the stimulation still is not tolerable, then the process can change the duty cycle and frequency again 1058. If the stimulation is found to be tolerable, the parameters are recorded 1059 or 1060. When the stimulation is being delivered with a 200 µS pulse width (e.g. Sets 2 or 4), the amplitude of the current can be incrementally increased until it reaches the 6 mA safety limit for Sets 2 or 4, as illustrated at 1054.

The present subject matter refers to neural stimulation. Neural stimulation may be delivered in a manner that stimulates neural activity in the target nerve or in a manner that inhibits or blocks neural activity in the target nerve. The present subject matter is applicable to either neural stimulation or inhibition.

As will be understood by one of ordinary skill in the art upon reading and comprehending the present subject matter, various embodiments of the present subject matter improve patient acceptance of therapy, maintain efficacious levels of therapy, allow patient flexibility in therapy management, and generally improve the quality of life of the patient who is receiving the NCT. The modules and other circuitry shown and described herein can be implemented using software, hardware, firmware and combinations thereof.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A neural stimulator, comprising:
    controller circuitry;
    neural stimulation output circuitry configured to deliver the neural stimulation, wherein the controller circuitry is configured to control stimulation parameters of the neural stimulation delivered by the neural stimulation output circuitry;
    sensor circuitry, including at least one sensor, configured to sense a response to the neural stimulation, wherein the controller circuitry is configured to communicate with the sensor circuitry;
    a memory with instructions operable on by the controller circuitry, wherein the controller circuitry is configured to operate on the instructions to:
        deliver neural stimulation using the neural stimulation output circuitry;
        control a titration sweep, wherein the titration sweep varies stimulation parameter values among a limited number of defined parameter sets, wherein each of the defined parameter sets is associated with a defined safety limit that determines a maximum current for a given one of the defined parameter sets, and wherein the instructions for controlling the titration sweep include instructions for changing current amplitude up to the maximum current, and changing to at least one other parameter set from the limited number of defined parameter sets; and
        monitor a response to the titration sweep including monitor for a desirable response indicative of efficacious neural stimulation and an undesirable response indicative of intolerable neural stimulation, the instructions for controlling the titration sweep being responsive to monitored responses; and
        use the monitored response to automatically select a defined parameter set from the limited number of defined parameter sets, and use the automatically-selected defined parameter set to automatically select stimulation parameters that provide an efficacious neural stimulation and provide a desirable safety margin to prevent injury to neural tissue, wherein the automatically-selected stimulation parameters include a current value that does not exceed the maximum current for the automatically-selected parameter set and do not violate neural stimulation safety limits for a charge per phase or a charge density per phase.

2. The neural stimulator according to claim 1, wherein the controller is configured to operate on the instructions to calculate the safety limit for the stimulation parameters, and confirm that the charge per phase and charge density per phase does not violate the safety limit.

3. The neural stimulator of claim 1, wherein the controller is configured to operate on the instructions to calculate changes to a current amplitude, a pulse width and a frequency among the limited number of defined parameter sets during the titration sweep, and control the neural stimulation output circuitry to control changes to the current amplitude, the pulse width and the frequency during the titration sweep.

4. The neural stimulator of claim 1, further comprising an input connected to the controller circuitry and configured to receive a patient tolerance input signal indicative of whether the neural stimulation is intolerable, wherein the controller circuitry is configured to use the patient tolerance input signal to control the titration sweep.

5. The neural stimulator of claim 4, wherein the input is configured to receive a communication signal from a programmer, wherein the programmer is configured to be used by a clinician to program the neural stimulator and to receive an entry from the clinician regarding patient tolerance to the neural stimulation.

6. The neural stimulator of claim 1, wherein the controller is configured to operate on the instructions to increment current amplitude until the current amplitude reaches the maximum current, and change pulse width when the maximum current is reached.

7. The neural stimulator of claim 1, wherein the controller is configured to operate on the instructions to select a defined parameter set that maximize the safety margin for the parameter sets evaluated during the titration sweep.

8. The neural stimulator of claim 1, wherein the memory includes the limited number of parameter sets.

9. The neural stimulator of claim 1, wherein the neural stimulation output circuitry is configured to adjust current amplitude and is further configured to adjust at least one parameter selected from the group of parameters consisting of: a pulse width, a stimulation frequency, an electrode configuration and a dose of the neural stimulation.

10. The neural stimulator of claim 1, wherein the neural stimulator is configured to provide a consistent dose of neural stimulation, and each of the defined parameter sets include selected neural stimulation parameters to provide the consistent dose of neural stimulation.

11. The neural stimulator of claim 1, wherein the controller is configured to operate on the instructions to control changes to a pulse width among the limited number of defined parameter sets during the titration sweep.

12. The neural stimulator of claim 1, wherein the controller is configured to operate on the instructions to control changes to a frequency among the limited number of defined parameter sets during the titration sweep.

13. The neural stimulator of claim 1, further comprising an input connected to the controller circuitry and configured to receive a patient tolerance input signal indicative of whether the neural stimulation is intolerable, wherein the controller circuitry is configured to use the patient tolerance input signal to control the titration sweep, wherein the input is configured to receive a communication signal from an external device that is configured to be used by a patient, wherein the external device is configured to receive an entry from the patient regarding patient tolerance to the neural stimulation.

14. A neural stimulator, comprising:
controller circuitry;
neural stimulation output circuitry configured to deliver the neural stimulation, wherein the controller circuitry is configured to control stimulation parameters of the neural stimulation delivered by the neural stimulation output circuitry, wherein the neural stimulation output circuitry is configured to adjust current amplitude and is further configured to adjust at least one parameter selected from the group of parameters consisting of: a pulse width, a stimulation frequency, an electrode configuration and a dose of the neural stimulation;
sensor circuitry, including at least one sensor, configured to sense a response to the neural stimulation, wherein the controller circuitry is configured to communicate with the sensor circuitry;
a memory with instructions operable on by the controller circuitry, wherein the controller circuitry is configured to operate on the instructions to:
deliver neural stimulation using the neural stimulation output circuitry;
control a titration sweep, wherein the titration sweep varies stimulation parameter values among a limited number of defined parameter sets, wherein each of the defined parameter sets is associated with a defined safety limit that determines a maximum current for a given one of the defined parameter sets, and wherein the instructions for controlling the titration sweep include instructions for changing current amplitude up to the maximum current, and changing to at least one other parameter set from the limited number of defined parameter sets; and
monitor a response to the titration sweep including monitor for a desirable response indicative of efficacious neural stimulation and an undesirable response indicative of intolerable neural stimulation, the instructions tier controlling the titration sweep being responsive to monitored responses; and
use the monitored response to automatically select a defined parameter set from the limited number of defined parameter sets, and use the automatically-selected defined parameter set to automatically select stimulation parameters that provide an efficacious neural stimulation and provide a desirable safety margin to prevent injury to neural tissue, wherein the automatically-selected stimulation parameters include a current value that does not exceed the maximum current for the automatically-selected parameter set and do not violate neural stimulation safety limits for a charge per phase or a charge density per phase; and
an input connected to the controller circuitry and configured to receive a patient tolerance input signal indicative of whether the neural stimulation is intolerable, wherein the controller circuitry is configured to use the patient tolerance input signal to control the titration sweep, wherein the input is configured to receive a communication signal from an external device that is configured to be used by a patient, wherein the external device is configured to receive an entry from the patient regarding patient tolerance to the neural stimulation.

15. The neural stimulator of claim 14, wherein the memory includes the limited number of parameter sets.

16. The neural stimulator of claim 14, wherein the controller is configured to operate on the instructions to control changes to a pulse width among the limited number of defined parameter sets during the titration sweep.

17. The neural stimulator of claim 14, wherein the controller is configured to operate on the instructions to control changes to a frequency among the limited number of defined parameter sets during the titration sweep.

18. The neural stimulator of claim 14, wherein the controller is configured to operate on the instructions to calculate the safety limit for the stimulation parameters, and confirm that the charge per phase and charge density per phase does not violate the safety limit.

19. The neural stimulator of claim 14, wherein the controller is configured to operate on the instructions to calculate changes to a current amplitude, a pulse width and a frequency among the limited number of defined parameter sets during the titration sweep, and control the neural stimulation output circuitry to control changes to the current amplitude, the pulse width. and the frequency during the titration sweep.

20. The neural stimulator of claim 14, further comprising an input connected to the controller circuitry and configured to receive a patient tolerance input signal indicative of whether the neural stimulation is intolerable, wherein the controller circuitry is configured to use the patient tolerance input signal to control the titration sweep.

* * * * *